(12) United States Patent
Gee

(10) Patent No.: US 11,944,739 B2
(45) Date of Patent: Apr. 2, 2024

(54) ERGONOMIC PHACOEMULSIFICATION HANDPIECE WITH A LEVER FOR INDEPENDENT NEEDLE AND SLEEVE ROTATION

(71) Applicant: Johnson & Johnson Surgical Vision, Inc., Irvine, CA (US)

(72) Inventor: Jacob Gee, Blanchester, OH (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 681 days.

(21) Appl. No.: 17/038,685

(22) Filed: Sep. 30, 2020

(65) Prior Publication Data

US 2021/0007891 A1 Jan. 14, 2021

Related U.S. Application Data

(63) Continuation-in-part of application No. PCT/IB2020/054646, filed on May 15, 2020.
(Continued)

(51) Int. Cl.
*A61F 9/007* (2006.01)
*A61M 1/00* (2006.01)
(Continued)

(52) U.S. Cl.
CPC .......... *A61M 1/774* (2021.05); *A61F 9/00745* (2013.01); *A61M 3/0283* (2013.01);
(Continued)

(58) Field of Classification Search
CPC ... A61F 9/00745; A61M 3/0283; A61M 1/77; A61M 2210/0612; A61M 1/774;
(Continued)

(56) References Cited

U.S. PATENT DOCUMENTS 4,180,074 A 12/1979 Murry et al.
4,504,264 A 3/1985 Kelman
(Continued)

FOREIGN PATENT DOCUMENTS

DE 19819432 A1 * 11/1999 .......... A61M 1/0064
WO 2011008672 A2 1/2011
WO 2019202530 A1 10/2019

OTHER PUBLICATIONS

International Search Report for Application No. PCT/IB2020/054646 dated Jul. 23, 2020, 2 pages.

*Primary Examiner* — Kelly J Bekker
*Assistant Examiner* — Andrew P. Restaino
(74) *Attorney, Agent, or Firm* — Johnson & Johnson Surgical Vision, Inc.

(57) ABSTRACT

An apparatus, system and method for a phacoemulsification handpiece. The phacoemulsification handpiece may include: a proximal portion having a longitudinal axis, and a first end and a second end, wherein at least aspiration, irrigation and power connectors couple with the first end; a distal portion along the longitudinal axis and comprising a coupling configured to couple a needle with the distal portion; and a lever connectively associated with the coupling extending outwardly from the coupling through the distal portion, wherein actuation of the outwardly extending aspect of the lever provides a rotation of the coupling independent of rotation of the distal portion.

16 Claims, 9 Drawing Sheets

Related U.S. Application Data

(60) Provisional application No. 62/849,792, filed on May 17, 2019.

(51) Int. Cl.
*A61M 3/02* (2006.01)
*A61B 17/00* (2006.01)

(52) U.S. Cl.
CPC .............. *A61B 2017/00398* (2013.01); *A61B 2017/0042* (2013.01); *A61B 2017/00424* (2013.01); *A61B 2217/005* (2013.01); *A61B 2217/007* (2013.01); *A61M 1/77* (2021.05)

(58) Field of Classification Search
CPC .. A61B 2017/00398; A61B 2017/0042; A61B 2017/00424; A61B 2217/005; A61B 2217/007
See application file for complete search history.

(56) References Cited

U.S. PATENT DOCUMENTS

| | | | |
|---|---|---|---|
| 5,162,044 A | 11/1992 | Gahn et al. | |
| 5,342,293 A | 8/1994 | Zanger | |
| 5,413,556 A | 5/1995 | Whittingham | |
| 5,453,087 A | 9/1995 | Malinowski | |
| 5,609,602 A | 3/1997 | Machemer et al. | |
| 5,653,724 A | 8/1997 | Imonti | |
| 5,843,109 A | 12/1998 | Mehta et al. | |
| 6,086,554 A * | 7/2000 | Humphreys, Jr. | A61M 1/774 |
| | | | 604/35 |
| D441,863 S | 5/2001 | Khalaj et al. | |
| 6,852,092 B2 | 2/2005 | Kadziauskas et al. | |
| 7,169,123 B2 | 1/2007 | Kadziauskas et al. | |
| D724,726 S | 3/2015 | Prokop | |
| D753,823 S | 4/2016 | Hayamizu | |
| D795,424 S | 8/2017 | Sloss | |
| D870,264 S | 12/2019 | Fedor et al. | |
| D871,574 S | 12/2019 | Lohk et al. | |
| D871,575 S | 12/2019 | Lohk et al. | |
| D871,576 S | 12/2019 | Lohk et al. | |
| D879,290 S | 3/2020 | Harman et al. | |
| D886,999 S | 6/2020 | Lohk et al. | |
| D888,237 S | 6/2020 | Lohk et al. | |
| D898,910 S | 10/2020 | Hansen et al. | |
| D909,575 S | 2/2021 | Ohno | |
| D946,146 S | 3/2022 | Gee et al. | |
| 2001/0018570 A1 | 8/2001 | Sussman et al. | |
| 2005/0277970 A1* | 12/2005 | Norman | A61B 17/32002 |
| | | | 606/180 |
| 2006/0079832 A1 | 4/2006 | Akahoshi | |
| 2008/0161720 A1* | 7/2008 | Nicoson | A61B 17/3421 |
| | | | 600/567 |
| 2008/0294087 A1 | 11/2008 | Steen et al. | |
| 2009/0005712 A1 | 1/2009 | Raney | |
| 2010/0069825 A1 | 3/2010 | Raney | |
| 2010/0228119 A1 | 9/2010 | Brennan et al. | |
| 2011/0009874 A1 | 1/2011 | Wardle et al. | |
| 2011/0137231 A1 | 6/2011 | Sorensen et al. | |
| 2012/0078234 A1 | 3/2012 | Merchant et al. | |
| 2015/0133946 A1* | 5/2015 | Horvath | A61M 27/002 |
| | | | 606/108 |
| 2016/0038342 A1 | 2/2016 | Van et al. | |
| 2018/0333165 A1* | 11/2018 | Algawi | A61B 17/32002 |
| 2019/0321017 A1 | 10/2019 | Christopher et al. | |
| 2021/0100574 A1* | 4/2021 | Magno | A61B 17/32002 |
| 2022/0096270 A1 | 3/2022 | Brady | |
| 2022/0192879 A1 | 6/2022 | Gee | |

* cited by examiner

ERGONOMIC PHACOEMULSIFICATION HANDPIECE WITH A LEVER FOR INDEPENDENT NEEDLE AND SLEEVE ROTATION

CROSS-REFERENCE TO RELATED APPLICATIONS

This application claims priority to and is a continuation-in-part of PCT Application No. PCT/IB2020/054646, filed May 15, 2020, which claims priority to U.S. provisional application No. 62/849,792, filed May 17, 2019, which are incorporated herein by reference in their entirety.

FIELD OF THE DISCLOSURE

The field of the invention relates to a handpiece, and more particularly to an apparatus, system and method for ergonomic phacoemulsification handpieces.

BACKGROUND OF THE DISCLOSURE

A cataract is an opacity that develops in the lens of an eye. Cataracts are the most significant cause of blindness worldwide. Phacoemulsification is a medically recognized technique utilized for crystalline lens removal, which is a highly prevalent method of treating cataracts.

Phacoemulsification includes emulsifying, or liquefying, the cataractic lens through a corneal and/or scleral incision. A phacoemulsification system 5 known in the art is shown in FIG. 1. The system 5 generally includes a phacoemulsification handpiece 10 coupled to an irrigation source 30 and more or more aspiration pumps, e.g. pump 40, for insertion into the eye through the incision.

The handpiece 10 includes a distal tip (i.e., a needle) 15 (shown within the anterior chamber of the patient's eye 1) that emits ultrasonic energy to emulsify the cataractic lens within the patients eye 1. The handpiece 10 further includes: a sleeve 26 that surrounds at least a portion of needle 15, and which provides one or more irrigation ports 25 proximal to the distal tip 15 that are coupled to an irrigation source 30 via an irrigation line 35; and an aspiration port 20 at the distal tip 15 which is coupled to aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirated from the eye 1 by the aspiration pump 40 via the aspiration port 20 and the aspiration line 45.

Turning to FIG. 2, a functional block diagram of a phacoemulsification system 100 known in the art is shown. The system 100 includes a control unit 102 and a handpiece 104 operably coupled together. The control unit 102 generally controls the operating parameters of the handpiece 104, e.g., the rate of aspiration A, rate of irrigation (or flow) F, and power P applied to the needle, and hence the eye E. The control unit 102 generally includes a microprocessor computer 110 which is operably connected to and controls the various other elements of the system 100.

The control unit 102 may include an aspiration pump, such as a Venturi (or vacuum-based pump) or a variable speed pump (or a flow based or peristaltic pump) 112, for providing a vacuum/aspiration source, which, in the case of a variable speed pump 112, can be controlled by a pump speed controller 116. The unit 102 further includes an ultrasonic power source 114 and an ultrasonic power level controller 118 for controlling the power P applied to the needle 15 of the handpiece 104. A vacuum sensor 120 provides an input to the computer 110 representing the vacuum level on the output side of the pump 112. Venting may be provided by a vent 122.

The system 100 may also include a phase detector 124 for providing an input to the computer 100 that represents the phase between a sine wave representation of the voltage applied to the handpiece 104 and the resultant current into the handpiece 104. The functional representation of the system 100 also includes a system bus 126 to enable the various elements to be operably in communication with each other.

Turning to FIG. 3, the cross-section along the longitudinal axis of a portion of a phacoemulsification handpiece 200 known in the art is shown. Generally, the handpiece 200 includes a needle 210, defining a lumen that is operatively coupled to an aspiration pump (e.g. aspiration pump 40 (FIG. 1)), forming an aspiration line 214. At least a portion of the distal end of needle 210 is surrounded by sleeve 220 and proximal end of the needle 210 is coupled to a horn 250, which has its proximal end coupled to a set of piezoelectric crystals 280, shown as three rings. The horn 250, crystals 280, and a proximal portion of the needle 210 are enclosed within a handpiece casing 270 having an irrigation port coupled to an irrigation line 290 defining an irrigation pathway 295. Irrigation pathway 295 extends between the wall of sleeve 220 and the wall of needle 210, allowing fluid to flow around needle 210 and exit one or more ports 225 in sleeve 220. The irrigation line 290 is coupled to the irrigation source 30 (FIG. 1).

The horn 250 is typically an integrated metal, such as titanium, structure and often includes a rubber O-ring 260 around the mid-section, just before the horn 250 tapers to fit with the needle 210 at the horn's 250 distal end. The O-ring 260 snugly fits between the horn 250 and the casing 270. The O-ring 260 seals the proximal portion of the horn 250 from the irrigation pathway 295. Thus, there is a channel of air defined between the horn 250 and the casing 270. Descriptions of handpieces known in the art are provided in U.S. Pat. No. 6,852,092 (to Kadziauskas et al.) and U.S. Pat. No. 5,843,109 (to Mehta et al.), which are hereby incorporated by reference in their entirety.

In preparation for operation, a sleeve 220 is typically added to the distal end of the handpiece 200, covering the proximal portion of the needle 210 (thus, exposing the distal tip of the needle), and the distal end of the irrigation pathway 295, thereby extending the pathway 295 and defining an irrigation port 222 and/or port 225 just before the distal tip of the needle 210. The needle 210 and a portion of the sleeve 220 are then inserted through the cornea of the eye to reach the cataractic lens.

During operation, the irrigation path 295, the eye's chamber and the aspiration line 214 form a fluidic circuit, where irrigation fluid enters the eye's chamber via the irrigation path 295, and is then aspirated through the aspiration line 214 along with other materials that the surgeon desires to aspirate out, such as the cataractic lens. If, however, the materials, such as the cararactic lens, are too hard and massive to be aspirated through the aspiration line 214, then the distal end of the needle 210 is ultrasonically vibrated and applied to the material to be emulsified into a size and state that can be successfully aspirated.

The needle 210 is ultrasonically vibrated by applying electric power to the piezoelectric crystals 280, which in turn, cause the horn 250 to ultrasonically vibrate, which in turn, ultrasonically vibrates the needle 210. The electric power is defined by a number of parameters, such as signal frequency and amplitude, and if the power is applied in pulses, then the parameters can further include pulse width, shape, size, duty cycle, amplitude, and so on. These parameters are controlled by the control unit 102 and example control of these parameters is described in U.S. Pat. No. 7,169,123 to Kadziauskas et al.

With respect to FIG. 4, an exemplary handpiece known in the prior art is shown. As discussed above, the distal end 401 of the handpiece 400 is show with a tip/needle 404 and sleeve 403 having port 405. The proximal end 402 of the of the handpiece 400 comprises multiple ports/connector points 406, include a port 406a for connecting to the irrigation line, a port 406b for connecting to the aspiration line, and a connector port 406c for electrical power for the ultrasound.

The location of the ports/connector points 406 at the proximal end 402 of the handpiece 400 are known to create fatigue on the surgeon's hand and wrist due to the invariability in the orientation of the ports/connector points 406 in light of the rigidly correspondent weight of the proximal end 402 once the irrigation and aspiration lines and the power cord are connected to the handpiece (not shown). This fatigue from orienting the distal end of the handpiece results, in part and as shown in FIG. 4, from the typical construction of the handpiece as one-piece metal-type material. Consequently, to adjust or rotate the distal end of the phacoemulsification (phaco) tip/needle requires the entire handpiece and connected lines to be moved/rotated in unison to achieve the desired position.

With regard to achieving the desired position, the emulsifying needle is often bent or has a bevel edge, and thus must be properly positioned to achieve emulsification of the lens. Further, the irrigation ports on the handpiece are optimally oriented so as to direct fluid along the horizontal plane of the eye. As such, in the known art, the surgeon will frequently rotate the handpiece such that the needle tip is at whatever angle is most proper to remove the cataract material, but unfortunately, due to the afore-discussed construction of the typical phacoemulsification handpiece, this rotation of the needle also executes a correspondent rotation away from the optimal position for the irrigation ports.

This need to move/rotate the entire handpiece also creates fatigue to the surgeon's hand and/or wrist during surgery. As such, a new handpiece with features that address these drawbacks is needed.

Therefore, the need exists for a phacoemulsification handpiece that allows for ergonomic rotational movement of the emulsifying needle separately from movement of the sleeve.

SUMMARY

The disclosure is and includes an apparatus, system and method for a phacoemulsification handpiece. The phacoemulsification handpiece may include: a proximal portion having a longitudinal axis, and a first end and a second end, wherein at least aspiration, irrigation and power connectors couple with the first end; a distal portion along the longitudinal axis and comprising a coupling configured to couple a needle with the distal portion; and a lever connectively associated with the coupling and extending outwardly from the longitudinal axis through the distal portion. Actuation of the outwardly extending aspect of the lever then provides a rotation of the coupling independent of rotation of the distal portion.

The handpiece may additionally include a second segment body along the longitudinal axis and comprising, at a distalmost portion thereof from the first segment: an emulsifying needle vibrated by a transducer powered by the power input, the transducer residing within the second segment body and being associated with a horn proximate the first segment; and an irrigation sleeve including an irrigation output. A grip may be about the proximal portion of the lever, and may be associated with the irrigation sleeve. At least one low friction interface may be present between an underside of the grip and the horn.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the disclosure. Moreover, in the figures, like reference numerals may or may not designate corresponding parts throughout the different views. Moreover, all illustrations are intended to convey concepts, where relative sizes, shapes and other detailed attributes may be illustrated schematically rather than literally or precisely. More specifically, in the drawings.

DETAILED DESCRIPTION

Figure 1:
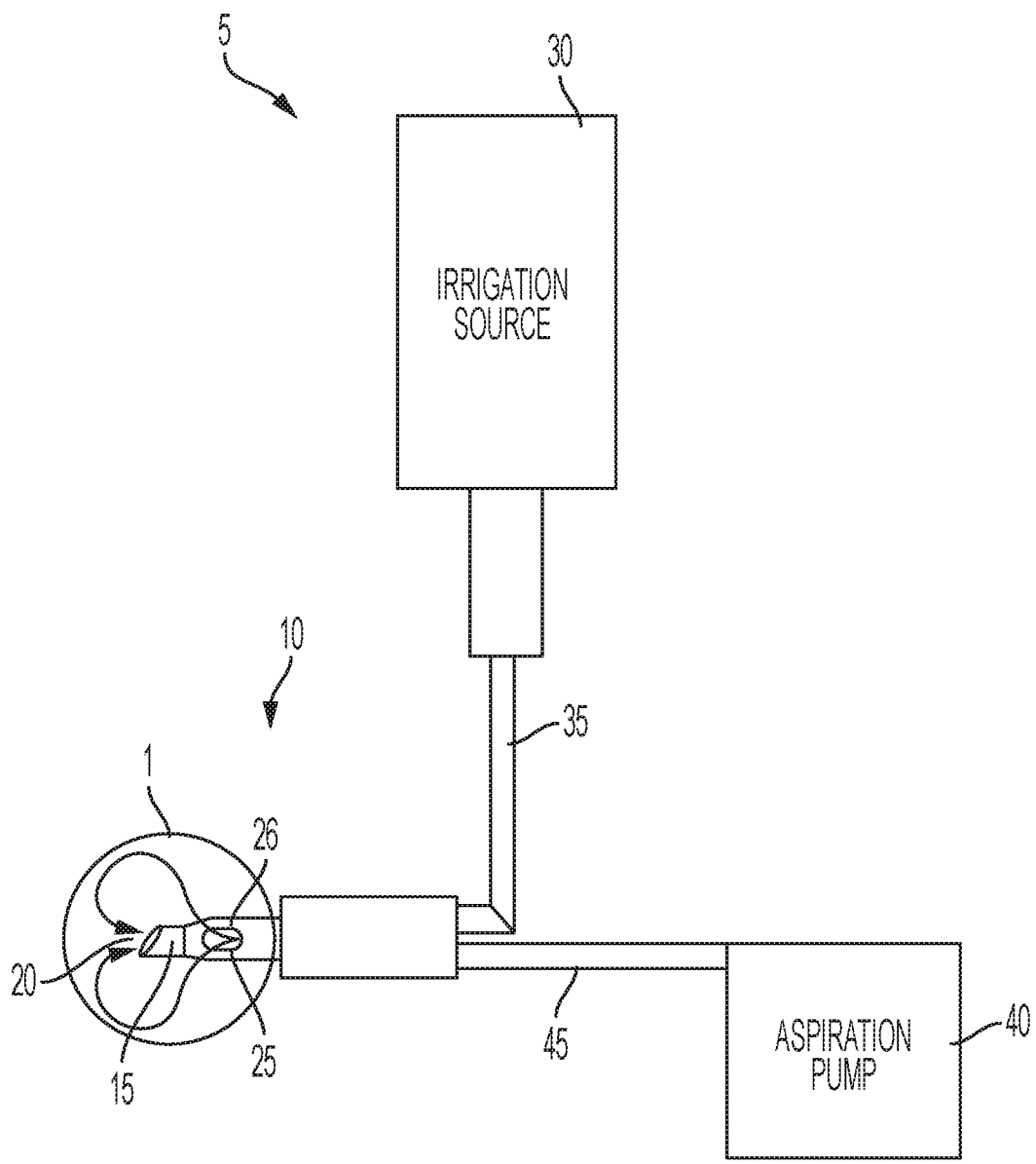
FIG. 1 is a diagram of a phacoemulsification system known in the art.
Figure 2:
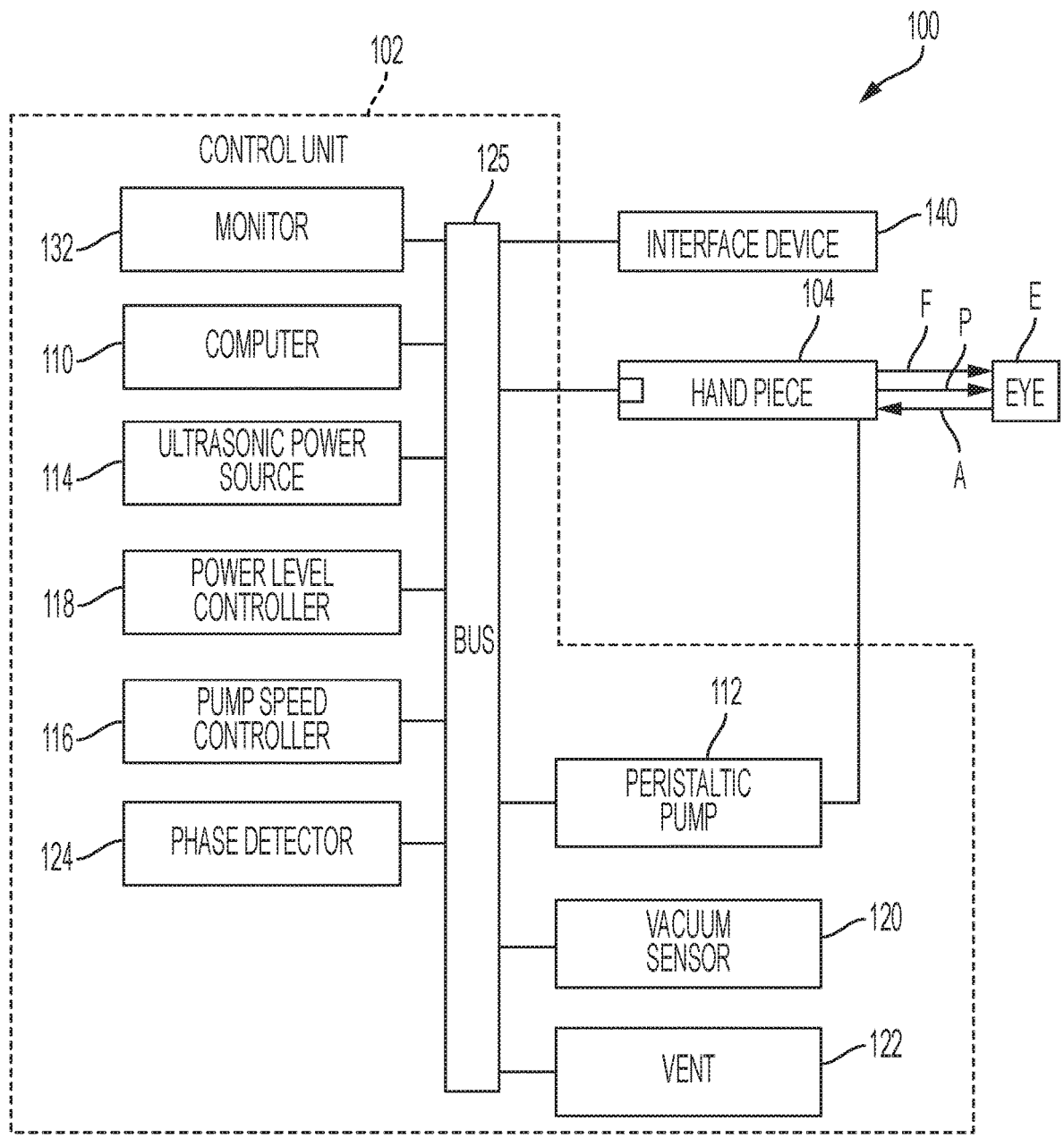
FIG. 2 is another diagram of a phacoemulsification system known in the art.
Figure 3:
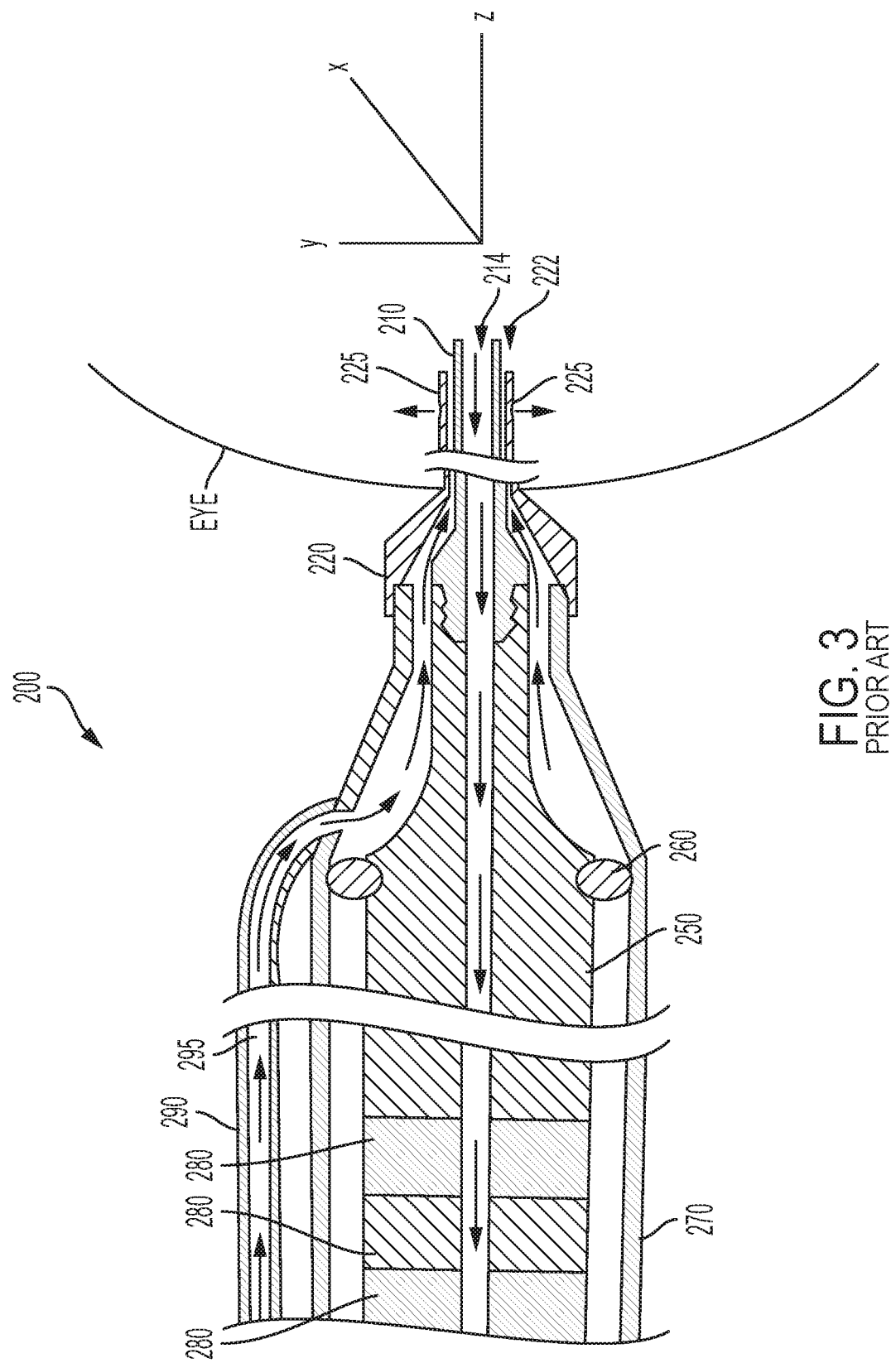
FIG. 3 is a diagram of a phacoemulsification handpiece known in the art.
Figure 4:
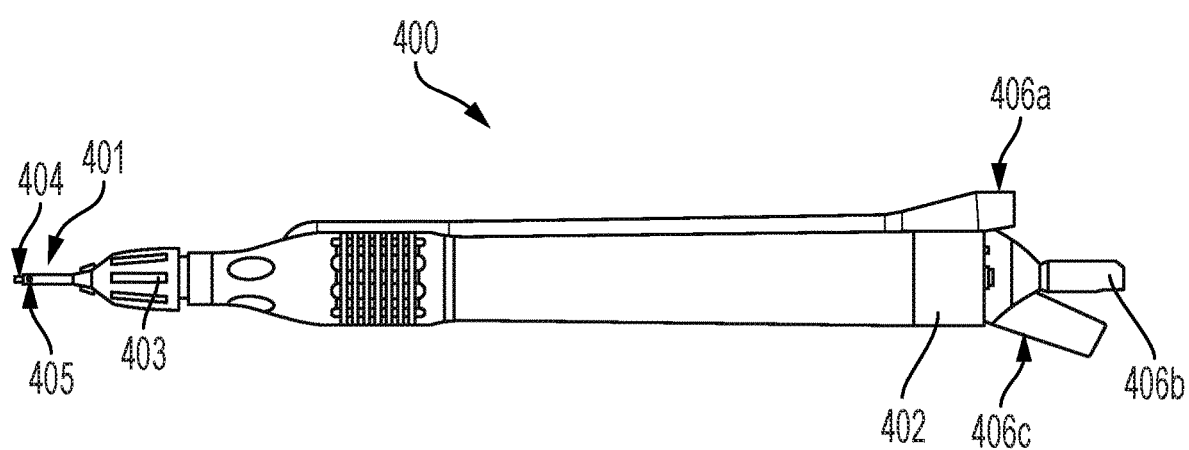
FIG. 4 is an example of a phacoemulsification handpiece known in the art.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical surgical, and particularly ophthalmic surgical, devices, systems, and methods. Those of ordinary skill may thus recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements or aspects, these elements or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, component, region, layer or section discussed below could be termed a second element, component, region, layer or section without departing from the teachings of the disclosure.

Certain types of ocular dysfunction, such as cataracts, are commonly treated with the surgical procedures referenced above, wherein the natural lens is removed from the eye and replaced with a clear artificial intraocular lens (IOL). More specifically, as the lens is emulsified under a vacuum pull, it is aspirated from the eye. Also, during the procedure, irrigation fluid is administered into the eye as the emulsified material is aspirated, thereby maintaining pressure in the interior of the eye.

The embodiments herein may relate to a standard, rigid ultrasonic handpiece, as detailed above. Additionally, the embodiments may relate to a handpiece having a multi-directional, such as a flexurally moving, needle, or the embodiments may relate to a rotating handpiece.

More specifically, for each of the types of phacoemulsification handpieces referenced throughout—namely a standard, rigid handpiece, a rotationally-enabled handpiece, or a flexurally or multi-direction-capable handpiece—the embodiments provide ergonomic handpiece elements that allow for rotational movement of the emulsifying needle separately from movement of the irrigation sleeve, and/or of the needle and sleeve independently from the body of the handpiece. More particularly, the embodiments provide an external lever that controls rotation of at least the vibrating tip.

More specifically, in the known art the phacoemulsification needle and the irrigation sleeve and ports rotate together as the surgeon rotates the entire handpiece, as detailed above. The embodiments of the present invention include a grip coupled with the handpiece. The grip may be integral with, or distinct from and placed about, the distal portion of the handpiece. A lever extends outwardly through this grip, and is associated with a transducer, a horn, and/or a needle, such that actuation of this lever rotates at least the needle tip about a longitudinal axis of the handpiece. However, the rotation of the needle notwithstanding, the surgeon is able to hold on to the grip of the handpiece as the lever is actuated so as to maintain the irrigation sleeve, and/or the body of the handpiece, in a stationary position notwithstanding the rotation of at least the needle tip.

Thus, the disclosed handpiece may be axially stationary, and/or may operate flexurally, and/or may rotate around its center axis, while the surgeon may independently make fine movements of the tip using the finger-actuated lever. Therefore, the limited movement requirements of the cables on the end of the handpiece necessary to achieve the desired rotational position of the phacoemulsifying tip substantially reduce surgeon fatigue.

A rigid handpiece is detailed above. A rotationally enabled handpiece may have one or more rotatable segments in conjunction with managed, twistable cords and irrigation/aspiration lines, which allows for rotation of the phacoemulsification tip independent of these cords and lines.

In a flexurally-enabled handpiece, the ultrasonic horn may provide both longitudinal motion at the needle tip, and/or transversal/flexural motion at the needle tip, to emulsify the lens of the eye. The transversal motion provides a side-to-side or back-and-forth "sanding" motion at the tip to break up the lens and the longitudinal motion that causes any occluding particulate to move away from the tip.

Figure 5:
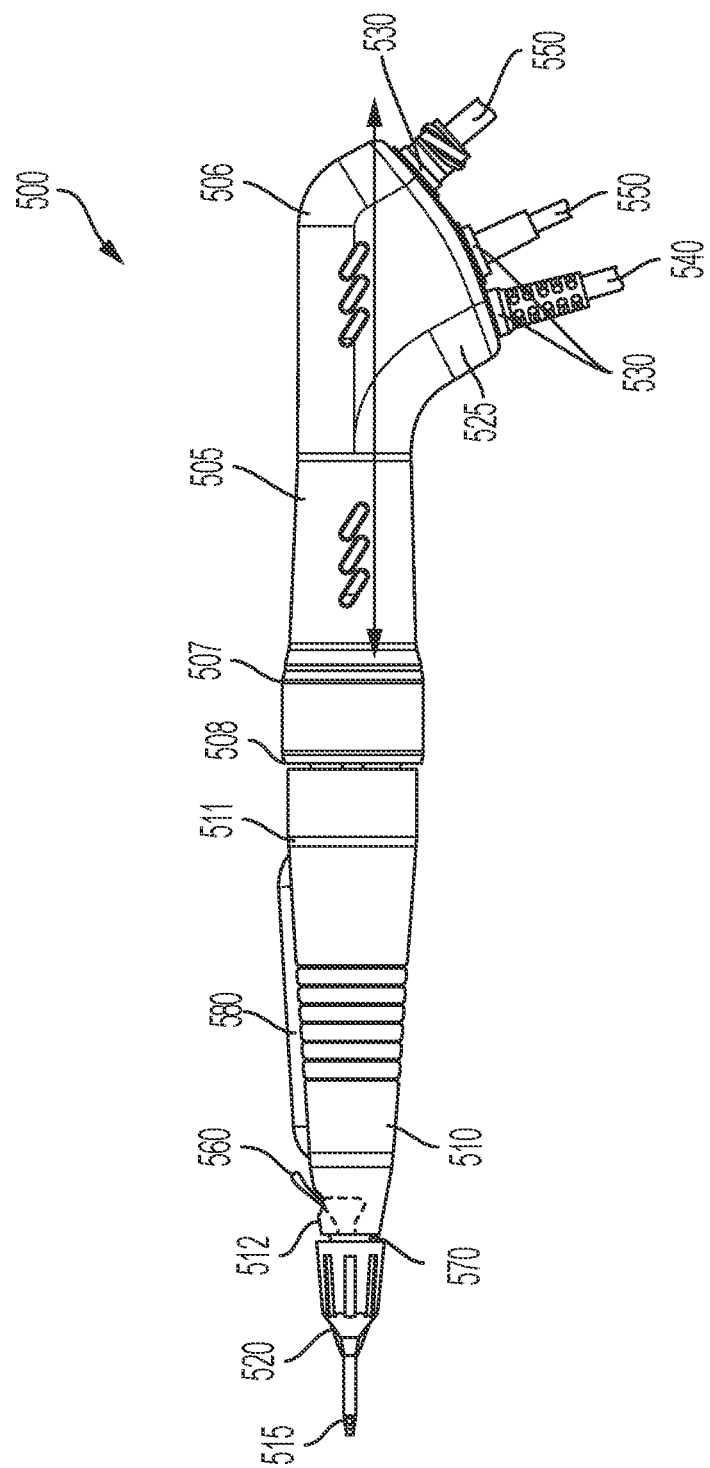
FIG. 5 shows an embodiment of a handpiece having a rotating tip.

By way of example of a rotationally-enabled handpiece, FIG. 5 illustrates that the handpiece 500 may have at least two segments, a proximal segment/portion 505 and a distal segment 510. Proximal segment 505 and distal segment 510 may be coupled to each other. Proximal segment 505 may have a first end 506 and a second end 507. Distal segment/portion 510 may have a first end 511 and a second end 512. Proximal segment 505 may be coupled to distal segment 510 via the first end 511 and second end 507. Proximal segment 505 and second segment 510 may be coupled together by coupler 508 using any means known in the art, including, but not limited to a low friction stainless steel bearing that freely allows axial rotation between the proximal segment 505 and the distal segment 510, such as axial rotation up to 350 degrees. In an embodiment, the axial rotation may be up to 180 degrees. In another embodiment, the axial rotation may be up to 90 degrees.

The coupler 508 may reside between the first end 511 and the second end 507. In addition, the at least one coupler 508 may be a part of the proximal segment 505 or the distal segment 510, and provides a swivel feature that allows proximal segment 505 and distal segment 510 to rotate independently of one another about an axis A. In an embodiment, the proximal and/or distal segments may be capable of rotating up to 359 degrees.

In an embodiment, the distal segment 510 of handpiece 500 may have a needle 515 connected to a distal-most portion of distal segment 510. A sleeve 520 may also be coupled with handpiece 500 and at least partially surround needle 515. Needle 515 and sleeve 520 may be separate components attachable to the distal segment 510 or may be integrally coupled with the distal segment 510 of handpiece 500. Proximal segment 505 of handpiece 500 includes tubing/cord management section 525 that includes one or more port/connector 530. The distal segment 510 includes a fluidics connector 580 (e.g., irrigation line). As shown in FIG. 5, for the fluidics connector to reach the sleeve 520, it must be routed around the rotating element 560.

Needle 515, or needle 515 and irrigation sleeve 520, may be coupled with a rotating element 560 on the distal segment 510. The distal segment 510 includes a coupling 570 that connects with the rotating element 560. By way of example, rotating element 560 may be the lever 560 shown. The lever 560 may be in communication with the transducer/horn 570 that vibrates needle 515 within the body of the distal segment 510, such as so as to rotate needle 515 upon actuation of lever 560 without rotation of other aspects of the handpiece 500. Alternatively, the lever 560 may be in communication with the irrigation sleeve 520, such as so as to rotate both the irrigation sleeve 520 and needle 515 upon actuation of lever 560.

The one or more port/connector 530 has cords 540 and/or tubing 550 connected thereto. In the known art, these connected cords 540 and/or tubing 550 lays or rests against a user's hand or wrist as the distal segment 510 is moved about.

Figure 6:
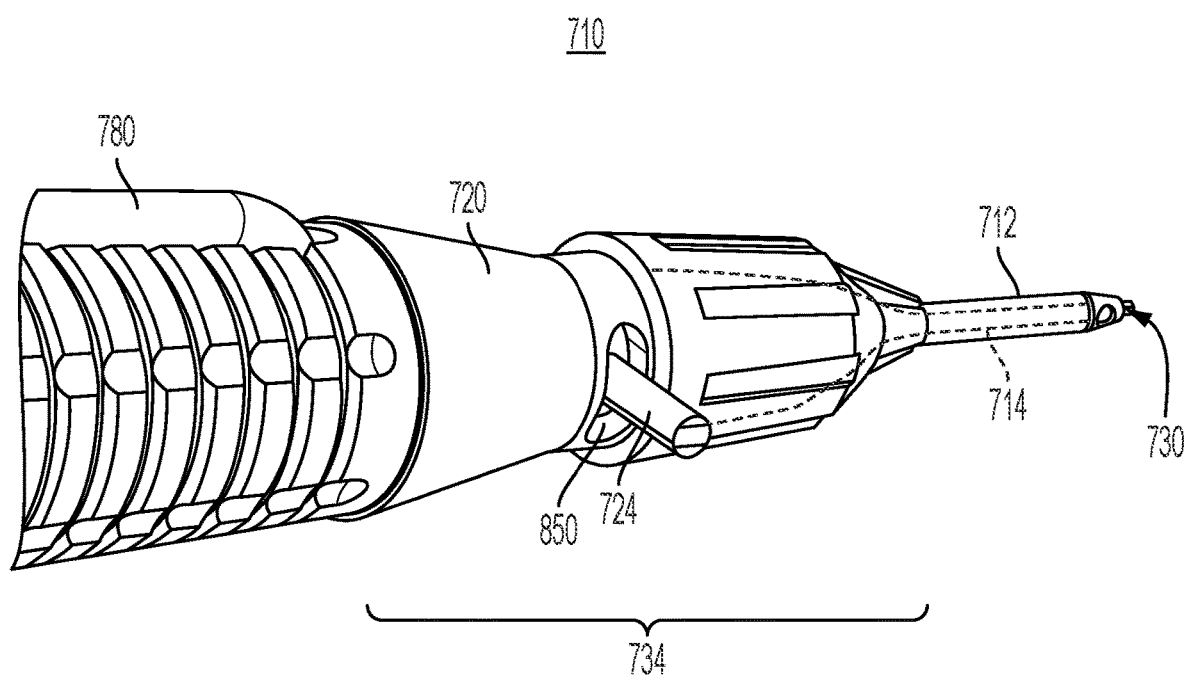
FIG. 6 shows an embodiment of a handpiece having a rotating tip.

FIG. 6 illustrates a phacoemulsification handpiece 710, which may be the rigid handpiece discussed above or a rotationally enabled handpiece 500 according to the embodiments. As illustrated in FIG. 6, an irrigation sleeve 712 is provided over a portion of needle 714 and/or a portion of the handpiece 710. In some embodiments, the sleeve 712 may be corresponded to a grip 720 in such a manner that the surgeon is able to hold on to the grip 720 to maintain the irrigation sleeve 712 in a substantially stationary position.

Also provided is a lever 724, such as may be actuatable by the application or pressure from a finger. Accordingly, a surgeon is able to use a finger on the lever 724 and other portions of a hand on the grip 720, in conjunction, in order to rotate the needle 714 and in particular, needle tip 730 connectively associated with the lever 724 independently from the irrigation sleeve 712, or with the irrigation sleeve independently from the body of the handpiece 710. The lever 724 may be formed of any hypoallergenic and readily-sterilizable substance, such as metal or plastic. The handpiece 710 includes a fluidics connector 780 (e.g., irrigation line). As shown in FIG. 6, for the fluidics connector 780 to reach the irrigation sleeve 712, it must be routed around a lever 724.

The grip 720 is shown to cover only a portion of the most distal end 734 of the handpiece 710 in the illustration. However, the skilled artisan will appreciate, in light of this disclosure, that the grip 720 may be extended to cover more of the handpiece 710, and/or may be more or less coextensive with the irrigation sleeve 712 and/or the tip 730.

As referenced, a lever 724 is shown as the aspect by which rotation is imparted to the emulsifying needle 730 independent of the grip 720. However, it will be appreciated that other manner of independent rotational elements may be used, rather than the lever 724. By way of example, a rotating wheel may partially or fully circumferentially extend beyond the grip perimeter, such that relative movement may be provided between the transducer/horn/needle and the grip.

Simply put, the handpiece 710 may thus include a coupling suitable to couple the rotation actuator 724 to the needle 730 in such a manner so as to allow for the needle 730 to be rotated, such as by actuation of lever 724. The coupling may be, for example, an aspect of the horn, of the handpiece casing, or the like. The sleeve 712 may couple with the handpiece and remain stationary upon rotation of the needle 730, or may rotate with the needle 730, by way of example.

Figure 7:
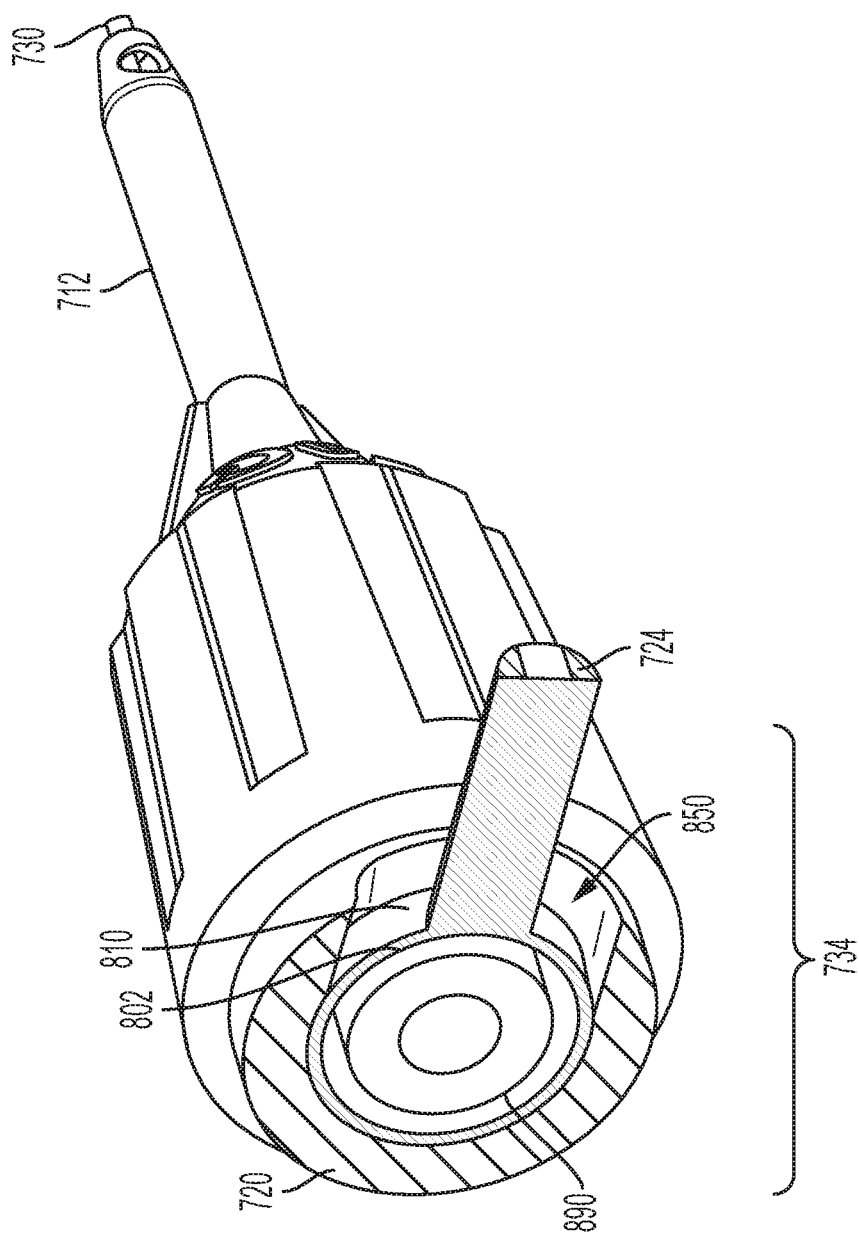
FIG. 7 shows an embodiment of a handpiece having a rotating tip.

FIG. 7 is a cross-sectional view of aspects of the disclosed embodiments. As shown, the rotating actuator 724, such as lever 724, may be attached to a coupling 890 associated with the handpiece 710, which coupling allows for the actuator 724 to impart rotation to the needle 730. By way of non-limiting example and as shown, the coupling 890 may be: an aspect of the transducer/transducer stack and/or the corresponding horn 802; a portion of the irrigation sleeve 712 extending inside the body of the handpiece; a dedicated casing within the body portion that encompasses the needle 730 or the needle 730 and sleeve 712; and/or a body portion of the handpiece 710 at the distal end thereof, so that at least the emulsifying needle 730 rotates from the coupling as the lever 724 is actuated.

More specifically, the coupling 890 may be composed of a uniformity between the lever and the horn 802 at point or points on the horn 802 distal from the needle tip 730. The lever 724 may thus be formed as part of the horn 802 to create the coupling, or may be otherwise attached to the horn 802, such as via glue or welding.

The irrigation sleeve 712, which additionally may include and/or cover one or more irrigation ports, may be attached independently to the grip 720. This attachment may be rigid, so as to longitudinally "lock" the sleeve's position and the grip's position. Alternatively, the sleeve 712 may be independent from the grip, and may be attached to the lever 724 in embodiments in which the sleeve 712 and needle are both configured to rotate independently from the body of the handpiece 710.

The grip 720 is fittedly placed over or coupled with at least a portion of the handpiece 710, as shown. This fitting may include a contouring of the grip 720 to aspects of the handpiece 710. Additionally, this fitting may include an aligning of a slot 850 to the lever 724, such that the lever 724 extends outwardly from the grip 720 to allow for actuation of the lever 724.

The grip 720, the distal end 734 of handpiece 710, and/or additional aspects/surfaces between the grip 720, the horn 802 and/or the distal end 734 with which grip 720 is coupled with, may include there-between a low friction surface 810, such as a plurality of bearings. This low friction surface may enable free independent rotation as between the grip 720, the distal end 734 of handpiece 710 over which the grip 720 may be fitted, and/or the horn 802 or other feature actuated by movement of lever 724.

Figure 8:
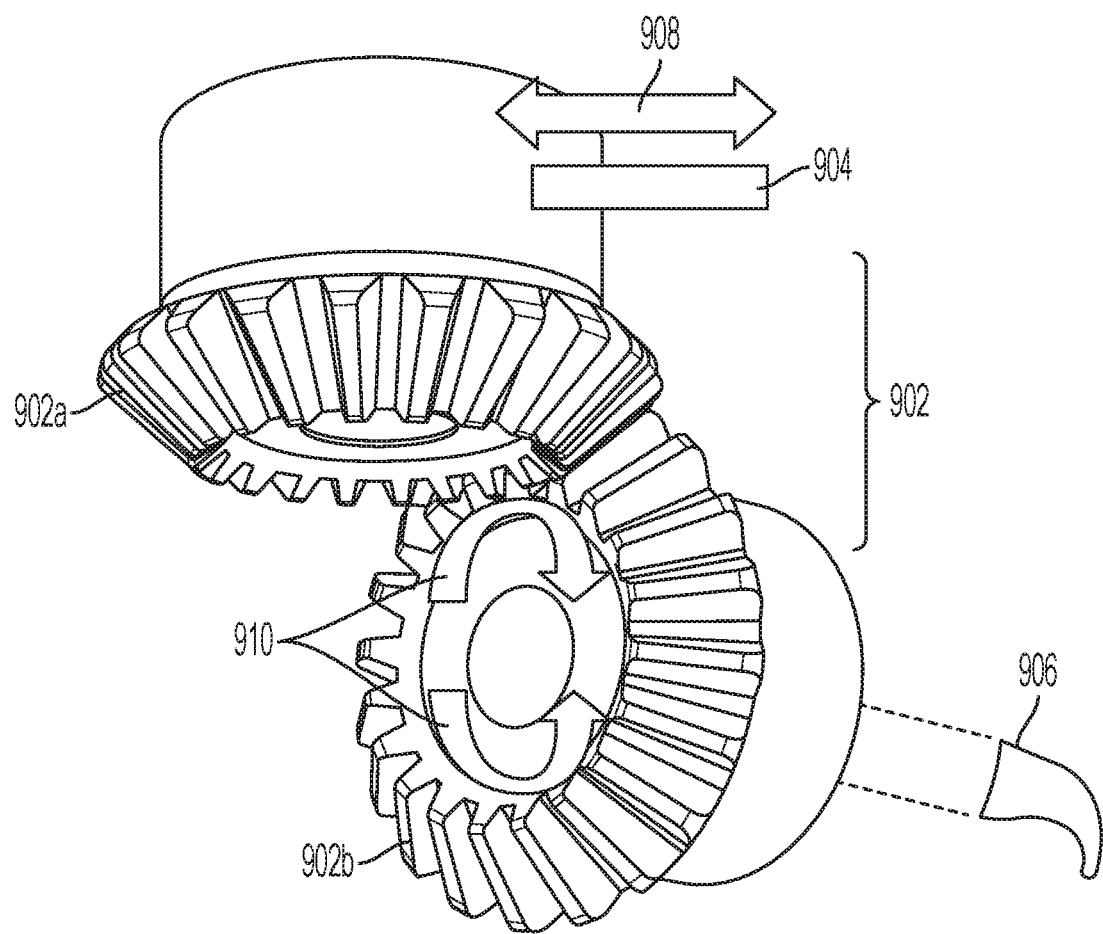
FIG. 8 shows an embodiment of a motion translation mechanism for a handpiece having a rotating tip.

FIG. 8 is an isometric view illustrating an embodiment of translation mechanism 902 capable of translating linear motion of the lever 904 into rotational motion of the phacoemulsification tip 906. Simply put, it may be logistically easier for a surgeon to move her fingertip forward and back, rather than side to side. A forward/back movement (as shown by arrow 908) of the disclosed lever may then drive a first translation element 902a, which communicates with a second translation element 902b of the translation mechanism 902 to translate the linear motion of the lever 904 into rotational motion of the tip 906.

The translation mechanism may thus be any combination of multiple translation elements suitable to provide the disclosed motion translation. By way of non-limiting example, the translation mechanism may be composed of a cam slot driven by movement of the lever, one or more gears or gear screws, and so on. FIG. 8 illustrates a first translation element 902a (e.g. a first gear) driven to rotate by linear movement of the lever 904 as shown, and a second translation element 902b (e.g. a second gear) that is communicative with the tip 906 and which is rotated (as shown by arrows 910) by the movement of the first gear. Accordingly, the simple gear system illustrated allows movement of the lever forward and backwards by the surgeon's finger to translate into rotation clockwise and counterclockwise of the tip.

Figure 9:
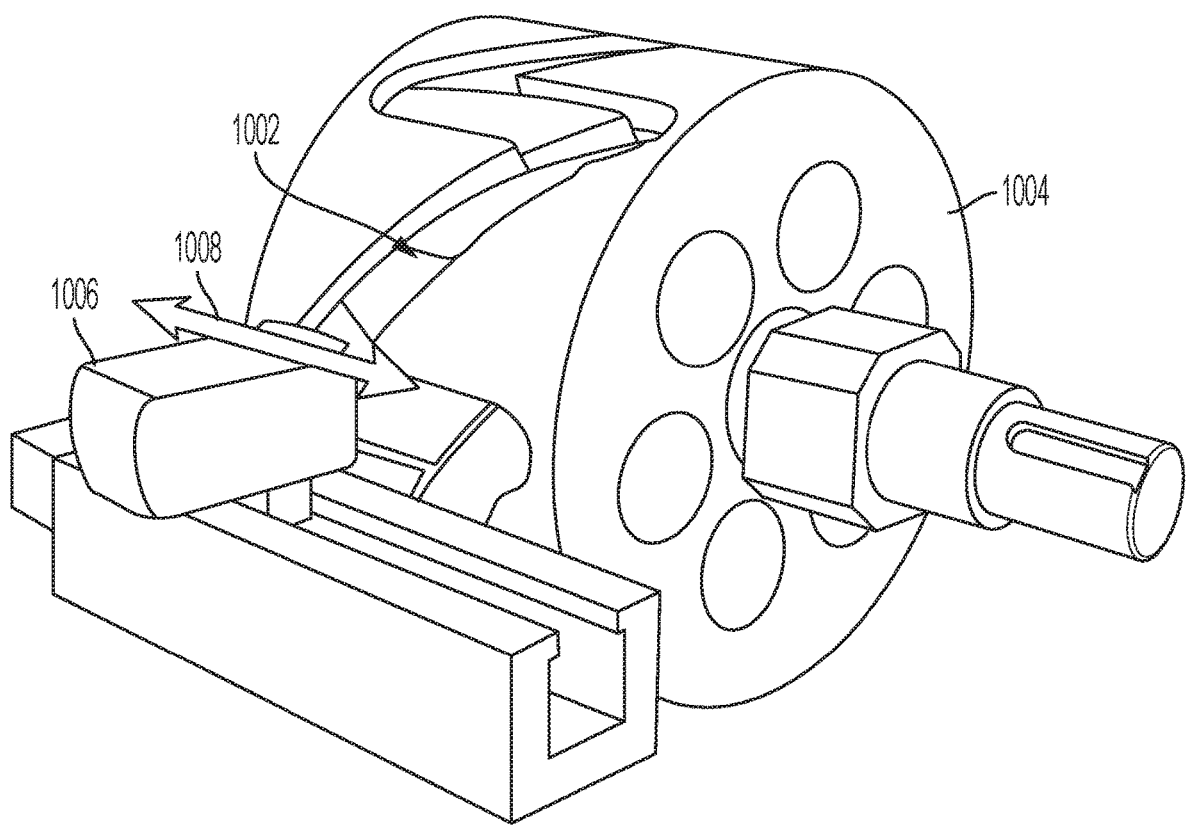
FIG. 9 shows an embodiment of a motion translation mechanism for a handpiece having a rotating tip.

FIG. 9 illustrates one of the foregoing exemplary translational movement embodiments. More particularly, a cam slot 1002 is illustrated on the horn 1004 that is associated with the tip. As shown, linear motion as shown by arrow 1008 on the lever 1006 is thus translated by the cam slot 1002 into rotational motion of the tip associated with the horn 1004.

Although the disclosure has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure.

What is claimed is:

1. A phacoemulsification handpiece comprising:
   a proximal portion having a longitudinal axis, and a first end and a second end, wherein an aspiration connector, an irrigation connector, and a power connector couple with the first end;
   a distal portion along the longitudinal axis and comprising a coupling configured to couple a needle with the distal portion;
   a lever connected with the coupling and extending outwardly from the longitudinal axis through the distal portion;
   wherein actuation of the outwardly extending aspect of the lever provides a rotation of the coupling independent of rotation of the distal portion;
   wherein a fluidic connection between the irrigation connector and an irrigation sleeve proximate the needle is routed around the coupling.

2. The handpiece of claim 1, wherein the connection between the lever and the coupling comprises a weld.

3. The handpiece of claim 1, wherein the coupling comprises a uniform body.

4. The handpiece of claim 1, wherein the needle comprises an aspiration port.

5. The handpiece of claim 1, further comprising a grip about the distal portion through which the lever extends outwardly.

6. The handpiece of claim 5, wherein the lever extends outwardly through a slot in the grip.

7. The handpiece of claim 5, wherein the association of the grip is with the irrigation sleeve in fluidic communication with the irrigation connector and is stationary in a longitudinal direction.

8. The handpiece of claim 7, wherein the irrigation sleeve is fitted to the grip.

9. The handpiece of claim 5, wherein the grip is fitted to the distal portion.

10. The handpiece of claim 5, further comprising at least one low friction interface on an underside of the grip proximate to the coupling, such that the low friction freely allows axial rotation between the proximal portion and the distal portion.

11. The handpiece of claim 1, further comprising a rotating coupler more proximal from the needle than the lever and being capable of coupling the proximal portion and the distal portion to enable independent axial rotation about the longitudinal axis of the proximal portion from the distal portion.

12. The handpiece of claim 1, wherein the proximal portion and the distal portion are stationary in relation to one another along the longitudinal axis.

13. The handpiece of claim 1, wherein rotation of the needle via the coupling is independent of movement of the proximal portion and the distal portion.

14. The handpiece of claim 1, wherein the needle is configured to be vibrated by a transducer powered by the power connector, the transducer residing within the proximal portion and being associated with a horn and the needle.

15. The handpiece of claim 14, wherein the transducer imparts multi-directional movement to the needle.

16. The handpiece of claim 1, wherein the coupling comprises a translation mechanism.

* * * * *